US010016582B2

(12) United States Patent
Hoekman et al.

(10) Patent No.: US 10,016,582 B2
(45) Date of Patent: Jul. 10, 2018

(54) CIRCUMFERENTIAL AEROSOL DEVICE

(71) Applicant: University of Washington through its Center for Commercialization, Seattle, WA (US)

(72) Inventors: John D. Hoekman, Seattle, WA (US); Rodney J. Y. Ho, Mercer Island, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 786 days.

(21) Appl. No.: 14/292,481

(22) Filed: May 30, 2014

(65) Prior Publication Data

US 2014/0343494 A1    Nov. 20, 2014

Related U.S. Application Data

(62) Division of application No. 12/866,448, filed as application No. PCT/US2009/033468 on Feb. 6, 2009, now Pat. No. 8,757,146.

(Continued)

(51) Int. Cl.
*A61M 11/00* (2006.01)
*A61M 31/00* (2006.01)
(Continued)

(52) U.S. Cl.
CPC ............ *A61M 31/00* (2013.01); *A61M 11/06* (2013.01); *A61M 15/00* (2013.01); *A61M 15/08* (2013.01);
(Continued)

(58) Field of Classification Search
CPC .... A61M 11/06; A61M 15/00; A61M 15/009; A61M 15/08; A61M 31/00;
(Continued)

(56) References Cited

U.S. PATENT DOCUMENTS 1,506,722 A * 8/1924 Yunker ................. B05B 1/3442
138/37
2,435,605 A * 2/1948 Rowell ................. B05B 1/3447
239/488
(Continued)

FOREIGN PATENT DOCUMENTS

DE         19518580 A1   11/1996
DE    10 2013 100 473 A1    7/2014
(Continued)

OTHER PUBLICATIONS

Extended European Search Report dated Jul. 1, 2015, issued in corresponding European Application No. 09707800.0, filed Feb. 6, 2009, 12 pages.
(Continued)

*Primary Examiner* — Peter S Vasat
*Assistant Examiner* — Margaret Luarca
(74) *Attorney, Agent, or Firm* — Christensen O'Connor Johnson Kindness PLLC

(57) ABSTRACT

The present application discloses devices and methods for delivering a therapeutic compound to the olfactory epithelium of an animal or human. The device having one or more channels for imparting a circumferential and axial velocity to the discharged fluid, and an outlet that discharges an aerosol spray having a circumferential and axial velocity as it enters the nasal cavity of a user. The device is designed to displace the air in the upper nasal cavity in order to specifically deposit a therapeutic agent on the olfactory epithelium while minimizing pressure and discomfort experienced by the user.

7 Claims, 14 Drawing Sheets

Related U.S. Application Data

(60) Provisional application No. 61/027,002, filed on Feb. 7, 2008.

(51) Int. Cl.
  *A61M 15/00* (2006.01)
  *A61M 15/08* (2006.01)
  *A61M 11/06* (2006.01)
  *B05B 7/08* (2006.01)
  *B05B 7/10* (2006.01)

(52) U.S. Cl.
  CPC .............. *B05B 7/0892* (2013.01); *B05B 7/10* (2013.01); *A61M 15/009* (2013.01); *A61M 2206/14* (2013.01); *A61M 2206/16* (2013.01)

(58) Field of Classification Search
  CPC .......... A61M 2206/14; A61M 2206/16; A61M 15/09; B05B 7/0892; B05B 7/10
  See application file for complete search history.

(56) References Cited

U.S. PATENT DOCUMENTS

| | | | |
|---|---|---|---|
| 3,888,253 A | 6/1975 | Watt et al. | |
| 3,906,950 A | 9/1975 | Cocozza | |
| 3,908,654 A | 9/1975 | Lhoest et al. | |
| 3,971,377 A | 7/1976 | Damani | |
| 4,095,596 A | 6/1978 | Grayson | |
| 4,187,985 A | 2/1980 | Goth | |
| 4,227,522 A | 10/1980 | Carris | |
| 4,353,365 A | 10/1982 | Hallworth et al. | |
| 4,412,573 A | 11/1983 | Zdeb | |
| 4,620,670 A | 11/1986 | Hughes | |
| 4,702,415 A | 10/1987 | Hughes | |
| 4,896,832 A | 1/1990 | Howlett | |
| 4,995,385 A | 2/1991 | Valentini et al. | |
| 5,224,471 A | 7/1993 | Marelli et al. | |
| 5,307,953 A | 5/1994 | Regan | |
| 5,331,954 A | 7/1994 | Rex et al. | |
| 5,349,947 A | 9/1994 | Newhouse et al. | |
| 5,382,236 A | 1/1995 | Otto et al. | |
| 5,398,850 A | 3/1995 | Sancoff et al. | |
| 5,435,282 A | 7/1995 | Haber et al. | |
| 5,505,193 A | 4/1996 | Ballini et al. | |
| 5,516,006 A | 5/1996 | Meshberg | |
| 5,711,488 A | 1/1998 | Lund | |
| 5,715,811 A | 2/1998 | Ohki et al. | |
| 5,797,390 A | 8/1998 | McSoley | |
| 5,814,020 A | 9/1998 | Gross | |
| 5,819,730 A | 10/1998 | Stone et al. | |
| 5,823,183 A | 10/1998 | Casper et al. | |
| 5,881,719 A | 3/1999 | Gottenauer et al. | |
| 5,901,703 A | 5/1999 | Ohki et al. | |
| 5,906,198 A | 5/1999 | Flickinger | |
| 5,910,301 A | 6/1999 | Farr et al. | |
| 5,954,696 A | 9/1999 | Ryan | |
| 6,062,213 A | 5/2000 | Fuisz et al. | |
| 6,092,522 A | 7/2000 | Calvert et al. | |
| 6,145,703 A | 11/2000 | Opperman | |
| 6,158,676 A | 12/2000 | Hughes | |
| 6,180,603 B1 | 1/2001 | Frey, II | |
| 6,186,141 B1 | 2/2001 | Pike et al. | |
| 6,189,739 B1 | 2/2001 | von Schuckmann | |
| 6,294,153 B1 | 9/2001 | Modi | |
| 6,302,101 B1 | 10/2001 | Py | |
| 6,313,093 B1 | 11/2001 | Frey, II | |
| 6,347,789 B1 | 2/2002 | Rock | |
| 6,367,471 B1 | 4/2002 | Genosar et al. | |
| 6,367,473 B1 | 4/2002 | Kafer | |
| 6,382,465 B1 | 5/2002 | Greiner-Perth | |
| 6,410,046 B1 | 6/2002 | Lerner | |
| 6,491,940 B1 | 12/2002 | Levin | |
| 6,540,983 B1 | 4/2003 | Adjei et al. | |
| 6,569,463 B2 | 5/2003 | Patel et al. | |
| 6,585,172 B2 | 7/2003 | Arghyris | |
| 6,585,957 B1 | 7/2003 | Adjei et al. | |
| 6,585,958 B1 | 7/2003 | Keller et al. | |
| 6,595,202 B2 | 7/2003 | Ganan-Calvo | |
| 6,622,721 B2 | 9/2003 | Vedrine et al. | |
| 6,644,305 B2 | 11/2003 | MacRae et al. | |
| 6,644,309 B2 | 11/2003 | Casper et al. | |
| 6,647,980 B1 | 11/2003 | Gizurarson | |
| 6,681,767 B1 | 1/2004 | Patton et al. | |
| 6,684,879 B1 | 2/2004 | Coffee et al. | |
| 6,701,916 B2 | 3/2004 | Mezzoli | |
| 6,715,485 B1 | 4/2004 | Djupesland | |
| 6,734,162 B2 | 5/2004 | Van Antwerp et al. | |
| 6,810,872 B1 | 11/2004 | Ohki et al. | |
| 6,923,988 B2 | 8/2005 | Patel et al. | |
| 7,033,598 B2 | 4/2006 | Lerner | |
| 7,051,734 B2 | 5/2006 | Casper et al. | |
| 7,063,686 B2 * | 6/2006 | Mezzoli | A61H 35/04 128/200.14 |
| 7,163,013 B2 | 1/2007 | Harrison | |
| 7,182,277 B2 | 2/2007 | Vedrine et al. | |
| 7,200,432 B2 | 4/2007 | Lerner et al. | |
| 7,214,209 B2 | 5/2007 | Mazzoni | |
| 7,231,919 B2 | 6/2007 | Giroux | |
| 7,258,119 B2 | 8/2007 | Mazzoni | |
| 7,296,566 B2 | 11/2007 | Alchas | |
| 7,347,201 B2 | 3/2008 | Djupesland | |
| 7,377,901 B2 | 5/2008 | Djupesland et al. | |
| 7,476,689 B2 | 1/2009 | Santus et al. | |
| 7,481,218 B2 | 1/2009 | Djupesland | |
| 7,484,678 B2 * | 2/2009 | Morrison | B05B 1/3442 239/302 |
| 7,543,581 B2 | 6/2009 | Djupesland | |
| 7,655,619 B2 | 2/2010 | During et al. | |
| 7,740,014 B2 | 6/2010 | Djupesland | |
| 7,784,460 B2 | 8/2010 | Djupesland et al. | |
| 7,799,337 B2 | 9/2010 | Levin | |
| 7,832,394 B2 | 11/2010 | Schechter et al. | |
| 7,841,337 B2 | 11/2010 | Djupesland | |
| 7,841,338 B2 | 11/2010 | Dunne et al. | |
| 7,854,227 B2 | 12/2010 | Djupesland | |
| 7,866,316 B2 | 1/2011 | Giroux | |
| 7,905,229 B2 | 3/2011 | Giroux et al. | |
| 7,934,503 B2 | 5/2011 | Djupesland et al. | |
| 7,975,690 B2 | 7/2011 | Djupesland | |
| 7,994,197 B2 | 8/2011 | Cook et al. | |
| 8,001,963 B2 * | 8/2011 | Giroux | A61M 15/08 128/200.14 |
| 8,047,202 B2 | 11/2011 | Djupesland | |
| 8,119,639 B2 | 2/2012 | Cook et al. | |
| 8,122,881 B2 | 2/2012 | Giroux | |
| 8,146,589 B2 | 4/2012 | Djupesland et al. | |
| 8,171,929 B2 | 5/2012 | Djupesland et al. | |
| 8,327,844 B2 | 12/2012 | Djupesland | |
| 8,408,427 B2 | 4/2013 | Wong | |
| 8,448,637 B2 | 5/2013 | Giroux | |
| 8,511,303 B2 | 8/2013 | Djupesland | |
| 8,517,026 B2 | 8/2013 | Amon | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,596,278 B2 | 12/2013 | Djupesland | |
| 8,733,342 B2 | 5/2014 | Giroux et al. | |
| 8,757,146 B2 | 6/2014 | Hoekman et al. | |
| 8,800,555 B2 | 8/2014 | Djupesland | |
| 8,839,790 B2 | 9/2014 | Arnon | |
| 8,875,794 B2 | 11/2014 | Carlsen et al. | |
| 8,899,229 B2 | 12/2014 | Djupesland et al. | |
| 8,899,230 B2 | 12/2014 | Immel | |
| 8,910,629 B2 | 12/2014 | Djupesland et al. | |
| 8,925,544 B2 | 1/2015 | Flickinger | |
| 8,978,647 B2 | 3/2015 | Djupesland et al. | |
| 8,987,199 B2 | 3/2015 | Maksoud et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,101,539 B2 | 8/2015 | Nagata et al. | |

(56) References Cited

U.S. PATENT DOCUMENTS

| | | | |
|---|---|---|---|
| 9,119,932 | B2 | 9/2015 | Djupesland |
| 9,180,264 | B2 | 11/2015 | Young et al. |
| 9,272,104 | B2 | 3/2016 | Djupesland |
| 9,446,207 | B2 | 9/2016 | Jung |
| 2002/0017294 | A1 | 2/2002 | Py |
| 2002/0054856 | A1 | 5/2002 | Jones |
| 2002/0092520 | A1 | 7/2002 | Casper et al. |
| 2003/0017119 | A1 | 1/2003 | Rabinowitz et al. |
| 2003/0158527 | A1 | 8/2003 | Mezzoli |
| 2003/0217748 | A1 | 11/2003 | Giroux |
| 2004/0068222 | A1 | 4/2004 | Brian |
| 2004/0238574 | A1 | 12/2004 | Merk et al. |
| 2005/0023376 | A1 | 2/2005 | Anderson |
| 2005/0028812 | A1 | 2/2005 | Djupesland |
| 2005/0036985 | A1 | 2/2005 | Ensoli |
| 2005/0098172 | A1 | 5/2005 | Anderson |
| 2005/0142072 | A1 | 6/2005 | Birch et al. |
| 2005/0274378 | A1 | 12/2005 | Bonney et al. |
| 2006/0107957 | A1 | 5/2006 | Djupesland |
| 2006/0219813 | A1 | 10/2006 | Morrison |
| 2006/0240092 | A1 | 10/2006 | Breitenkamp et al. |
| 2007/0056585 | A1 | 3/2007 | Davies et al. |
| 2007/0068514 | A1 | 3/2007 | Giroux |
| 2007/0074722 | A1 | 4/2007 | Giroux et al. |
| 2007/0119451 | A1 | 5/2007 | Wang et al. |
| 2007/0131224 | A1 | 6/2007 | Giroux |
| 2007/0172517 | A1 | 7/2007 | Ben-Sasson et al. |
| 2007/0202051 | A1 | 8/2007 | Schuschnig |
| 2008/0029084 | A1* | 2/2008 | Costantino ........... A61K 9/0043 128/200.14 |
| 2008/0054099 | A1 | 3/2008 | Giroux et al. |
| 2008/0163874 | A1 | 7/2008 | Djupesland |
| 2008/0178871 | A1 | 7/2008 | Genova et al. |
| 2008/0305077 | A1 | 12/2008 | Frey, II et al. |
| 2009/0320832 | A1 | 12/2009 | Djupestand |
| 2011/0053859 | A1 | 3/2011 | Deadwyler et al. |
| 2012/0195959 | A1 | 8/2012 | Ishii |
| 2014/0083424 | A1 | 3/2014 | Hoekman et al. |
| 2014/0170220 | A1 | 6/2014 | Cartt et al. |
| 2014/0343494 | A1 | 11/2014 | Hoekman et al. |
| 2015/0057287 | A1 | 2/2015 | Cook et al. |
| 2015/0216823 | A1 | 8/2015 | Chatterjee |
| 2015/0258178 | A1 | 9/2015 | Gong |
| 2016/0101245 | A1 | 4/2016 | Hoekman et al. |
| 2016/0228433 | A1 | 8/2016 | Haruta et al. |

FOREIGN PATENT DOCUMENTS

| | | |
|---|---|---|
| EP | 1165044 A2 | 1/2002 |
| GB | 806284 | 12/1958 |
| GB | 806284 A | 12/1958 |
| GB | 1517642 | 7/1978 |
| GB | 1517642 A | 7/1978 |
| JP | 8-322934 A | 12/1996 |
| JP | H08322934 A | 12/1996 |
| WO | 86/01731 A1 | 3/1986 |
| WO | 99/13930 A1 | 3/1999 |
| WO | 00/54887 A1 | 9/2000 |
| WO | 01/36033 A2 | 5/2001 |
| WO | 02/09707 A1 | 2/2002 |
| WO | 2007/007110 A1 | 1/2007 |
| WO | 2007/012853 A1 | 2/2007 |
| WO | 2008/059385 A2 | 5/2008 |
| WO | 2008/059385 A3 | 5/2008 |

OTHER PUBLICATIONS

Office Action dated Apr. 15, 2015, issued in corresponding Canadian Application No. 2,713,762, filed Feb. 6, 2009, 4 pages.

International Preliminary Report on Patentability dated Aug. 10, 2010, in corresponding International Application No. PCT/US2009/033468, filed Feb. 6, 2009, 7 pages.

International Search Report dated Dec. 2, 2009, issued in corresponding PCT/US2009/033468, filed Feb. 6, 2009.

Supplementary European Search Report dated Mar. 13, 2015, issued in corresponding European Application No. 09707800.0, filed Feb. 6, 2009, 6 pages.

Extended European Search Report dated Dec. 4, 2017, issued in corresponding European Application No. 17187144.5, filed Feb. 6, 2009, 11 pages.

Appasaheb, P.S., et al., "Review on Intranasal Drug Delivery System," Journal of Advanced Pharmacy Education and Research 3(4):333-346, Oct.-Dec. 2013.

Baron, E.P., and S.J. Tepper, "Orally Inhaled Dihydroergotamine: Reviving and Improving a Classic," Future Neurology 6(3):327-333, May 2011.

Constantino, H.R., et al., "Intranasal Administration of Acetylcholinesterase Inhibitors," BMC Neuroscience 9(Suppl 3):S6, Dec. 2008, 3 pages.

EP Search Report dated Jul. 1, 2015, for Application No. 09707800.0, filed Feb. 6, 2009, 12 pages.

EP Search Report dated Sep. 24, 2014, for Application No. 11818832.5, filed Aug. 19, 2011, 6 pages.

Hanson, L.R., and W.H. Frey II, "Intranasal Delivery of Growth Differentiation Factor 5 to the Central Nervous System," Drug Delivery 19(3):149-154, Feb. 2012.

Hoekman, J.D., "The Impact of Enhanced Olfactory Deposition and Retention on Direct Nose-to-Brain Drug Delivery," Doctoral Dissertation, University of Washington, Seattle, Wash., Apr. 11, 2011, 179 pages.

International Search Report dated Dec. 2, 2009, for International Application No. PCT/US2009/033468, filed Feb. 6, 2009, 5 pages.

Kumar, T.P., et al., "Nasal Drug Delivery: A Potential Route for Brain Targeting," Pharma Innovation Journal 2(1):77-85, Mar. 2013.

Ozsoy, Y., et al., "Nasal Delivery of High Molecular Weight Drugs," Molecules Journal 14:3754-3779, Sep. 2009.

Parvathi, M., "Intranasal Drug Delivery to Brain: An Overview," International Journal of Research in Pharmacy and Chemistry 2(3):889-895, 2012.

PCT Search Report and Written Opinion dated Mar. 27, 2012, for International Application No. PCT/US2011/048435, filed Aug. 19, 2011, 14 pages.

Renner, D.B., et al., "Intranasal Delivery of Insulin Via the Olfactory Nerve Pathway," Journal of Pharmacy and Pharmacology 64(12):1709-1714, Dec. 2012.

Stevens, J., et al., "Systemic and Direct Nose-to-Brain Transport Pharmacokinetic Model for Remoxipride After Intravenous and Intranasal Administration," Drug Metabolism and Disposition 39(12):2275-2282, Dec. 2011.

Talegaonkar, S., and P.R. Mishra, "Intranasal Delivery: An Approach to Bypass the Blood Brain Barrier," Indian Journal of Pharmacology 36(3):140-147, Jun. 2004.

Westin, U.E., et al., "Direct Nose-to-Brain Transfer of Morphine After Nasal Administration to Rats," Pharmaceutical Research 23(3):565-572, Mar. 2006.

Westin, U.E., "Olfactory Transfer of Analgesic Drugs After Nasal Administration," Digital Comprehensive Summaries of Uppsala Dissertations from the Faculty of Pharmacy 55, Uppsala University, Uppsala, Sweden, May 11, 2007, 66 pages.

Yamada, K., et al., "Nose-to-Brain Delivery of TS-002, Prostaglandin D2 Analogue," Journal of Drug Targeting 15(1):59-66, Jan. 2007.

Yimam, M.A., et al., "Effects of Lipid Association on Lomustine (CCNU) Administered Intracerebrally to Syngeneic 36B-10 Rat Brain Tumors," Cancer Letters 244(2):211-219, Dec. 2006.

Ying, W., "The Nose May Help the Brain: Intranasal Drug Delivery for Treating Neurological Diseases," Future Medicine 3(1):1-4, Jan. 2008.

Zhang, Q.-Z., et al., "The Brain Targeting Efficiency Following Nasally Applied MPEG-PLA Nanoparticles in Rats," Journal of Drug Targeting 14(5):281-290, Jun. 2006.

EP Ofice Action dated Nov. 9, 2016, for Application No. 14727320.5, filed Apr. 28, 2014, 6 pages.

Hanson, L.R. and W.H. Frey II, "Intranasal Delivery Bypasses the Blood-Brain Barrier to Target Therapeutic Agents to the Central

(56) References Cited

OTHER PUBLICATIONS

Nervous System and Treat Neurodegerative Disease," 2007 and 2008 Drug Discovery for Neurodegeneration Conference, New York, Feb. 5-6, 2007, BMC Neuroscience 9(Suppl 3), 2008, 4 pages.

* cited by examiner

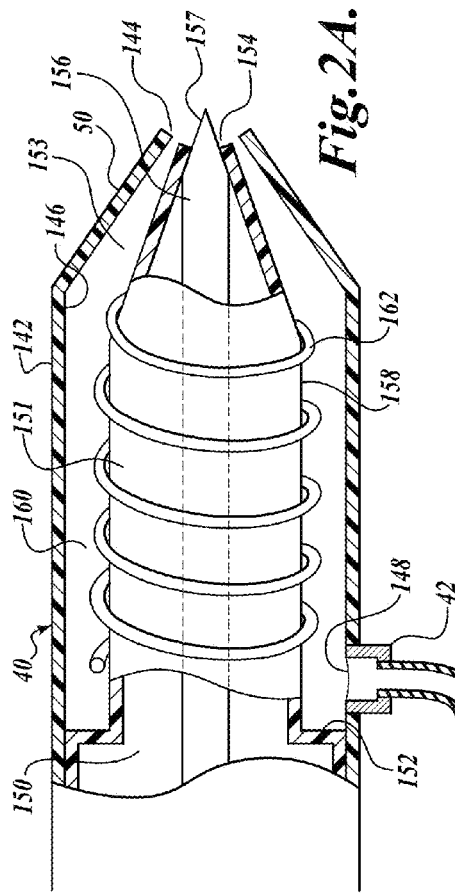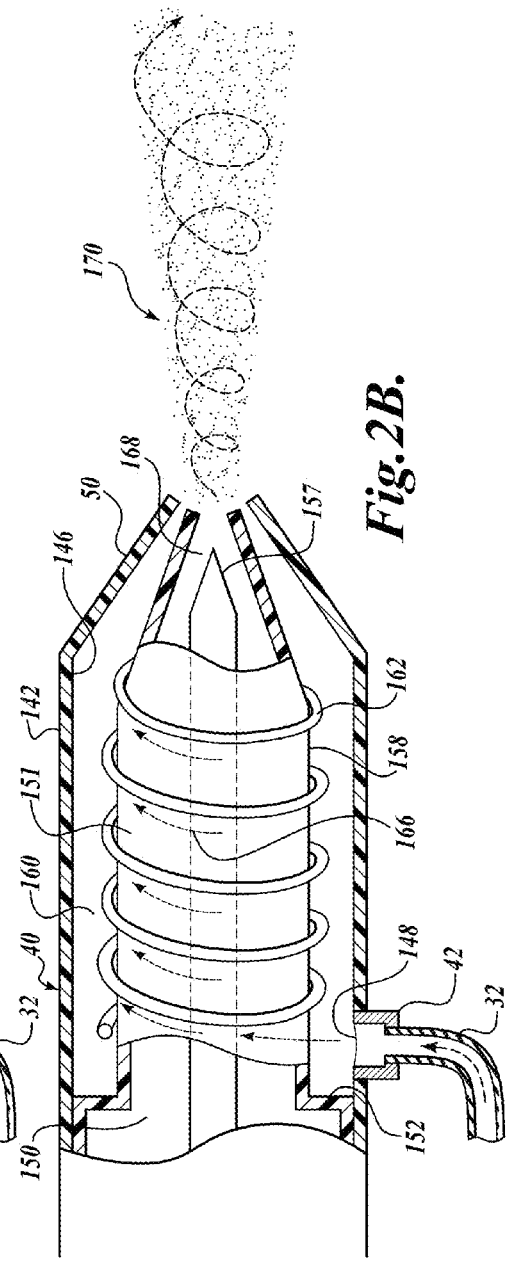

CIRCUMFERENTIAL AEROSOL DEVICE

CROSS-REFERENCES TO RELATED APPLICATIONS

This application is a division of U.S. patent application Ser. No. 12/866,448, filed Oct. 22, 2010, now U.S. Pat. No. 8,757,146, which is the national stage of International Application No. PCT/US2009/033468, filed Feb. 6, 2009, which claims the benefit of U.S. Provisional Patent Application No. 61/027,002, filed Feb. 7, 2008; each application is incorporated herein by reference in its entirety.

STATEMENT OF GOVERNMENT LICENSE RIGHTS

This invention was made with U.S. Government support under Grant Nos. AI052663 and 5R01AI77390-04 awarded by the National Institutes of Health (NIH). The U.S. Government has certain rights in the invention.

BACKGROUND

Depositing therapeutic drugs on the olfactory epithelium has been shown to lead to rapid and direct uptake into the brain. This direct nose-to-brain delivery route bypasses the blood-brain-barrier, which keeps a majority of drugs or drug candidates from reaching the brain in any significant concentrations. Many studies, including those of the present inventors, have shown that depositing a drug on the olfactory epithelium, while minimizing drug absorption on the respiratory epithelium, is key to maximizing the fraction of drug that bypasses the blood-brain-barrier and reaches the brain.

Currently there are no suitable nasal delivery devices that sufficiently target the olfactory region of the nasal cavity while avoiding the lungs and respiratory area of the nasal cavity. The olfactory region is a narrow space at the top of the nasal cavity taking up about 10% of the total surface area of the nasal cavity. In addition, when a subject breaths in through the nose, the inhaled air travels primarily along the lower part of the nasal cavity into the trachea and lung, thus, leaving the air in the olfactory region mainly undisturbed and stagnant in the olfactory region (and hence leading to a low fraction of olfactory drug exposure for drugs carried along the breath path).

The present disclosure overcomes the disadvantages associated with the anatomical impediments described above by providing pressurized olfactory drug delivery devices and methods for delivering pharmaceutical compounds to the olfactory epithelium.

SUMMARY

The present application discloses a pressurized olfactory drug delivery device for producing an aerosol nasal spray having a narrow spray plume with circumferential velocity. The device disclosed herein is designed to displace the residual olfactory air volume to deliver therapeutic compound to the olfactory region of the nasal cavity. In one aspect, the pressurized olfactory drug delivery device comprises a container having a mixture of a pressurized fluid and a therapeutic compound, a delivery device defining a longitudinal axis connected to the container and having an exit opening at the nasal-proximal end, a cylindrical channel connected to the outlet of the container and extending to the exit opening, and a plurality of discharge outlets radially disposed around the longitudinal axis, wherein each discharge outlet is oriented to discharge the pressurized fluid mixture in an axial and circumferential direction. The device further comprises a metering device for selectively discharging the pressurized fluid through the outlets, such that the outlets produce a plurality of aerosol spray discharges comprising the therapeutic compound that converge into a single spray plume having a circumferential helical velocity.

In a second aspect, the pressurized olfactory drug delivery device includes a container containing a mixture of a pressurized fluid and a therapeutic compound; a delivery device in communication with the container, the delivery device having a plurality of longitudinal helical channels, each helical channel comprising an inlet and an outlet disposed at the nasal proximal-most end of the device; and a metering device for selectively discharging the pressurized fluid mixture through the helical channels. The outlets are configured to discharge a plurality of aerosol spray jets comprising the pressurized fluid mixture that converge into a single spray plume having a circumferential helical velocity as the spray exits the device.

The present application also discloses a method for depositing a therapeutic compound on the olfactory epithelium in the nasal cavity of a human or animal subject, the method comprising administering a pressurized fluid comprising the therapeutic compound from a pressurized olfactory drug delivery device into the nasal cavity, wherein the device discharges a pressurized aerosol spray comprising the therapeutic compound, the pressurized aerosol spray having a circumferential velocity after exiting the device.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A is a partial cross sectional view of the nasal delivery device of FIG. 1;

FIG. 2B is a partial cross sectional view of the nasal delivery device of FIG. 1 in operation;

DETAILED DESCRIPTION

The present application discloses a pressurized olfactory drug delivery (PODD) device that produces an aerosol nasal spray having a narrow spray plume with circumferential velocity. The device disclosed herein is designed to displace the residual olfactory air volume under low pressure to increase the efficiency and consistency with which pharmaceutical compounds are delivered to olfactory epithelium, and further to enhance patient tolerability.

Figure 1:
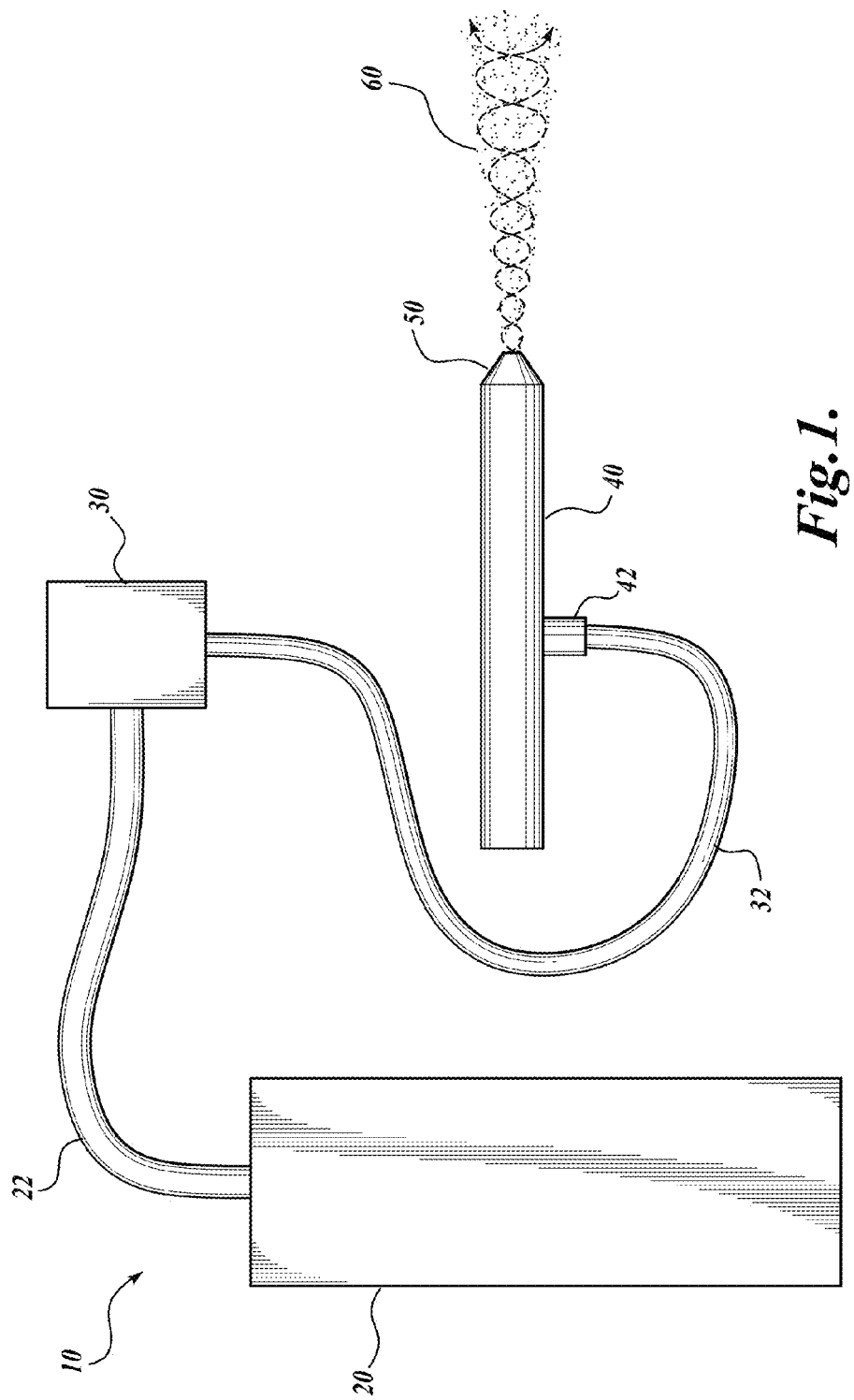
FIG. 1 is a schematic illustration of a pressurized olfactory drug delivery device constructed in accordance with one embodiment of the present disclosure.

A pressurized olfactory drug delivery device (PODD) 10 according to one embodiment of the present disclosure is best seen by referring to FIG. 1. The device 10 comprises a pressurized tank 20 suitable for storing a pressurized fluid, such as a compressed gas or propellant. The compressed gas may be compressed air, nitrogen, or any other suitable non-toxic gas. The propellant may be a pressurized fluid such as chlorofluorocarbon (CFC) or hydrofluoroalkane (HFA). The pressurized tank 20 is fluidically connected by tubing 22 to a pneumatic solenoid 30. The pneumatic solenoid 30 is fluidically connected by tubing 32 to an air chamber 42. The air chamber 42 is connected via an internal compartment to a nasal delivery device 40 having an applicator 50 with an orifice suitable for discharging an aerosol spray 60 into the nasal cavity of an animal subject. As used herein, the term aerosol refers to a suspension of fine solid or liquid particles in a gas, such as a mist.

Referring to FIG. 2A, the nasal delivery device 40 will now be described in detail. In one embodiment, the nasal delivery device 40 comprises a generally elongated tubular housing 142 having an exterior and interior and a first opening or orifice 144 at one end (the nasal proximal end) that is radially aligned about the longitudinal axis of the housing, the housing 142 being closed at the other end (the nasal distal end). The housing is preferably cylindrical in shape; however, any tubular shape may be used. The housing further comprises a conically shaped applicator 50 at the proximal end adjacent to and surrounding the orifice 144. The housing 142 surrounds a generally tubular, cylindrically shaped fluid reservoir 150 that extends along a portion of the longitudinal axis of the housing. The fluid reservoir has a proximal second orifice 154 disposed near the first orifice 144 of the housing, the second orifice 154 having a diameter smaller than that of the first orifice 144 and being generally radially aligned about the longitudinal axis of the housing 142. The proximal end is conically shaped adjacent to and surrounding the second orifice 154. The proximal portion 151 of the fluid reservoir 150 has a diameter narrower than the diameter of the housing 142, thereby forming a channel 153 extending from the distal portion of the reservoir 152 to the orifice 154. The distal portion 152 of the fluid reservoir 150 has a wider diameter, such that the exterior surface 158 of the fluid reservoir contacts the interior surface 146 of the housing 142, creating a seal that prevents flow of pressurized gas in a distal direction. The fluid reservoir 150 further comprises an elongated needle 156 whose long axis runs along the longitudinal axis of the housing 142 and is moveably disposed within the interior proximal portion of the fluid reservoir 150. The proximal end or tip 157 of the needle 156 is configured to seal the second orifice 154 of the fluid reservoir. The fluid reservoir 150 preferably is provided with a vent (not shown) to prevent a vacuum that would increase the pressure required to remove fluid from the second orifice 154.

The housing 142 further comprises a spin chamber 160 defined by the space between the interior surface 146 of the housing and the exterior surface 158 of the fluid reservoir. The housing further comprises a compressed gas inlet 148 that is in communication with the spin chamber 160 and fluidically connected to the pneumatic solenoid 30. The spin chamber further comprises a coiled wire 162 that is wrapped around the exterior 158 of the fluid chamber, the coiled wire 162 having a helical or corkscrew shape and extending from the gas inlet 148 to the proximal orifice 154.

Referring now to FIGS. 1 and 2B, the manner in which the embodiment of the PODD device 10 described above is used to deliver a pharmaceutical compound to the olfactory epithelium will now be described. When a user determines to discharge the pressurized nasal spray, the pneumatic solenoid 30 is activated by a programmable timer to release the pressurized gas from tank 20 for a predetermined amount of time. The pressurized gas released from the tank 20 travels through tubing 22, 32 to the air chamber 42 and through the air chamber 42 into the gas inlet 148 of the housing 142, thereby entering the spin chamber 160 of the nasal delivery device 40. The pressurized gas that enters the spin chamber 160 encounters the coiled wire 162, causing the pressurized gas 166 to flow around the exterior surface 158 of the fluid reservoir in a helical or corkscrew-shaped path, such that the gas acquires a circumferential helical velocity or vortex-like velocity having circumferential vector and axial vector components. The term circumferential velocity also includes tangential velocity, helical velocity, vortical velocity, and similar terms.

Referring now to FIG. 2B, when the solenoid 30 is activated, the elongated needle 156 disposed within the fluid reservoir 150 is retracted from the orifice 154, thereby providing a narrow opening 168 for the fluid within the fluid reservoir 150 to escape. As the pressurized gas 166 leaves the orifice 144, it creates a partial vacuum which forces fluid out of the reservoir 150 through the orifice 154. The fluid is aerosolized due to the narrowness of the gap 168. The aerosolized spray 170 is discharged from the nasal spray device 40 as a spray plume having a circumferential velocity and axial velocity as the spray plume enters the nasal cavity. The circumferential velocity has the advantage that the aerosol spray penetrates the upper nasal cavity allowing direct deposition of aerosolized therapeutic compounds on the olfactory epithelium.

The nasal delivery device can be used to deposit numerous types of therapeutic compounds and compositions on the olfactory epithelium, including neurological, analgesic, antiviral and cancer treatment compounds. Compounds that can be delivered include, but are not limited to, compounds comprising small molecular weight synthetic organic pharmaceuticals, peptide and protein therapeutic compounds, antibodies and antibody fragments, aptamer compounds, and DNA and RNA compounds. The compounds can be delivered as part of a composition or formulation to aid in stability or penetration of the olfactory epithelium. The composition may further comprise stabilizers, preservatives, or additives mixed with the therapeutic compound.

Figure 3:
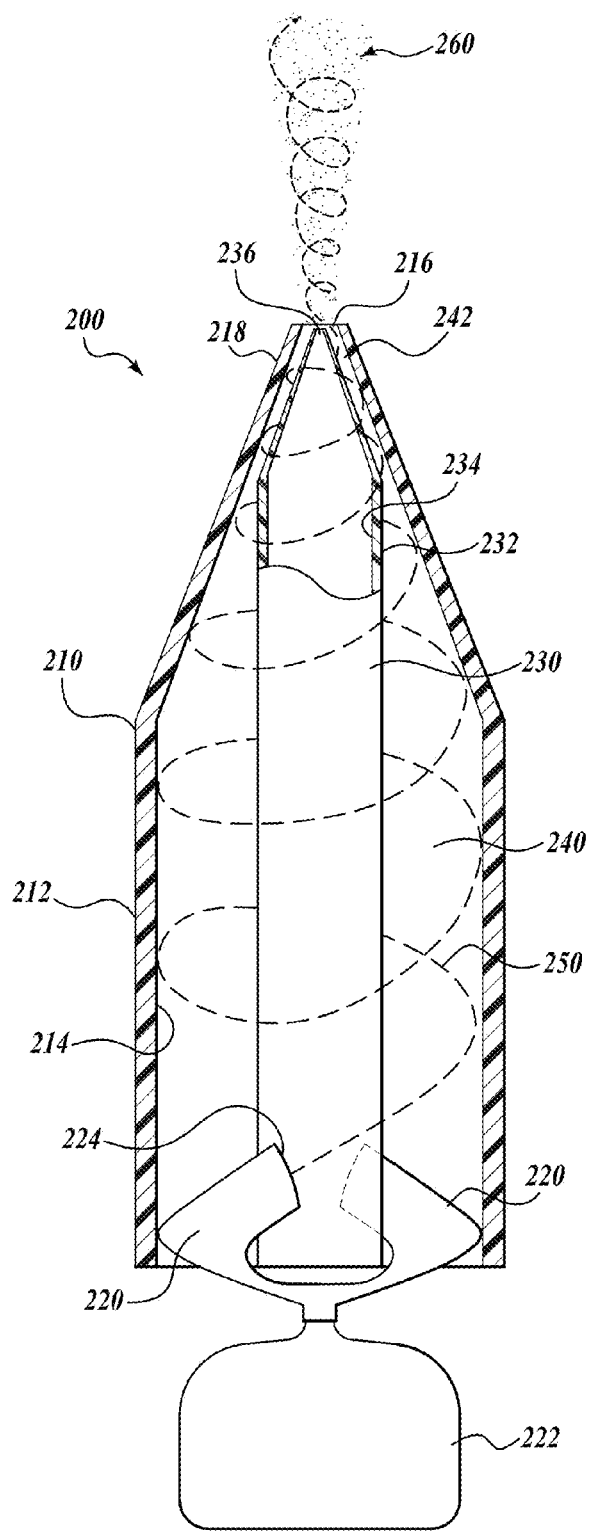
FIG. 3 is a partial cross sectional view of a pressurized olfactory drug delivery device according to a second embodiment of the present disclosure.

Referring to FIG. 3, a first alternate embodiment of a pressurized olfactory drug delivery device 200 will be hereinafter described. The device 200 comprises a tubular housing 210 having a central longitudinal axis, an exterior surface 212, an interior surface 214, and a first orifice 216 at the proximal end 218 thereof. The proximal end 218 of the housing 210 is preferably conically shaped to facilitate discharge of a pressurized nasal spray into the nasal cavity.

The device 200 further comprises a cylindrical fluid reservoir 230 that is radially disposed about the longitudinal axis and enclosed by the housing 210. The fluid reservoir 230 has an exterior surface 232 and an interior surface 234 and a second orifice 236 at the proximal end disposed near the first orifice 216 of the housing, the second orifice 236 having a diameter smaller than that of the first orifice 216 and being generally radially aligned about the longitudinal axis of the housing 210. The fluid reservoir 230 has a diameter narrower than the diameter of the housing 210. The proximal end of the fluid reservoir 230 is conically shaped adjacent to and surrounding the second orifice 236. The fluid reservoir 230 preferably is provided with a vent (not shown) to prevent a vacuum that would increase the pressure required to remove fluid from the second orifice 236.

The distal end of the housing 210 comprises one or more nozzles 220 that are fluidically connected to a compressed fluid container 222. The compressed fluid may be compressed air, compressed nitrogen, or a compressed propellant such as CFC or HFA, or any other suitable propellant recognized in the art. The compressed fluid container preferably has a metering device (not shown) to deliver a predetermined amount of fluid, gas or propellant when activated. In some embodiments, the compressed fluid container is a MDI. The proximal end of the nozzles 220 have openings 224 that open into a spin chamber 240 defined by the space between the exterior surface 232 of the fluid reservoir 230 and the interior surface 214 of the housing 210. The nozzles 220 are configured such that the openings 224 discharge the compressed fluid in a circumferential and axial direction, thereby establishing a circumferential velocity to the pressurized fluid.

With continued reference to FIG. 3, the manner in which the embodiment of the PODD device 200 described above is used to deliver a pharmaceutical compound to the olfactory epithelium will now be described. A user actuates the pressurized gas container 222 to release a predetermined amount of pressurized gas 250 into the spin chamber 240. The pressurized gas acquires a circumferential velocity having an axial and circumferential component and exits the first orifice 216. As the pressurized gas 250 leaves the first orifice 216, it creates a partial vacuum which forces fluid out of the reservoir 230 through the second orifice 236. The fluid is aerosolized due to the narrowness of the gap 242 defined by the interior surface 214 of the first orifice 216 and the exterior surface 232 of the fluid reservoir 230. The aerosolized spray is discharged from the nasal spray device 200, having a circumferential velocity as the aerosol spray 260 enters the nasal cavity.

Figure 4:
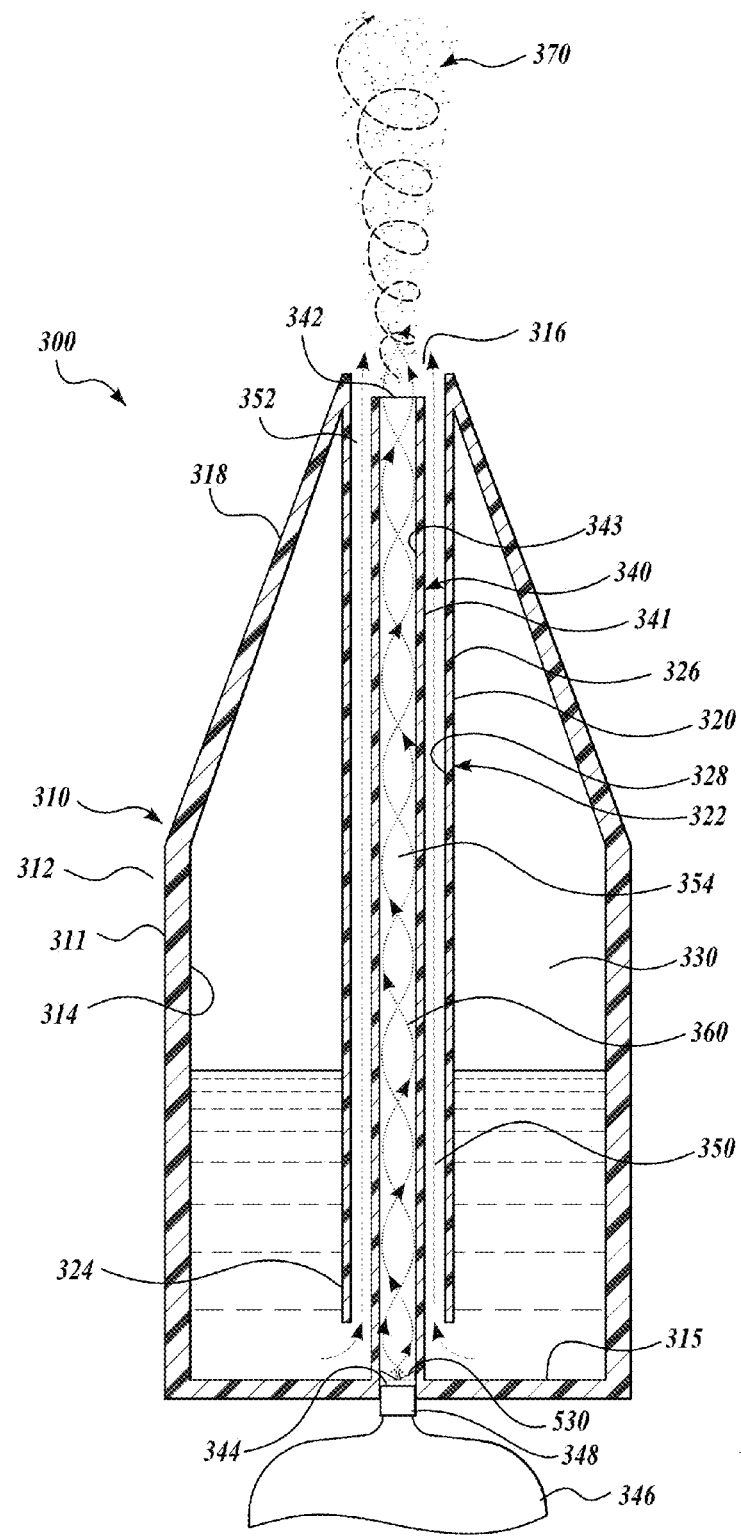
FIG. 4 is a cross sectional view of a pressurized olfactory drug delivery device according to a third embodiment of the present disclosure.

Referring now to FIG. 4, a second alternate embodiment of the pressurized drug delivery device 300 will be hereinafter described. The device 300 comprises a generally tubular cylindrical housing 310 having a central longitudinal axis, an outer wall 311 having an exterior surface 312 an interior surface 314, and a first orifice 316 at the nasal-proximal end 318. The proximal end 318 of the housing 310 is preferably conically shaped to enhance user comfort and facilitate discharge of a nasal spray into the nasal cavity.

The housing 310 further comprises an inner wall 320 defining an axially aligned inner cylinder 322 open at both ends and connected to the proximal end 318 of the housing 310 at the orifice 316 and having a distal open end 324 disposed near the interior surface 315 of the distal wall of the housing, thereby defining a sufficient gap for receiving a fluid between the distal open end 324 and the interior surface 315 of the wall. The inner cylinder 322 has a diameter less than the diameter of the outer wall 311, thereby defining a space between the exterior surface 326 of the cylinder 322 and the interior surface 314 of the outer wall 311 of the housing 310 that serves as a fluid reservoir 330 suitable for storing a liquid pharmaceutical composition.

Figure 5:
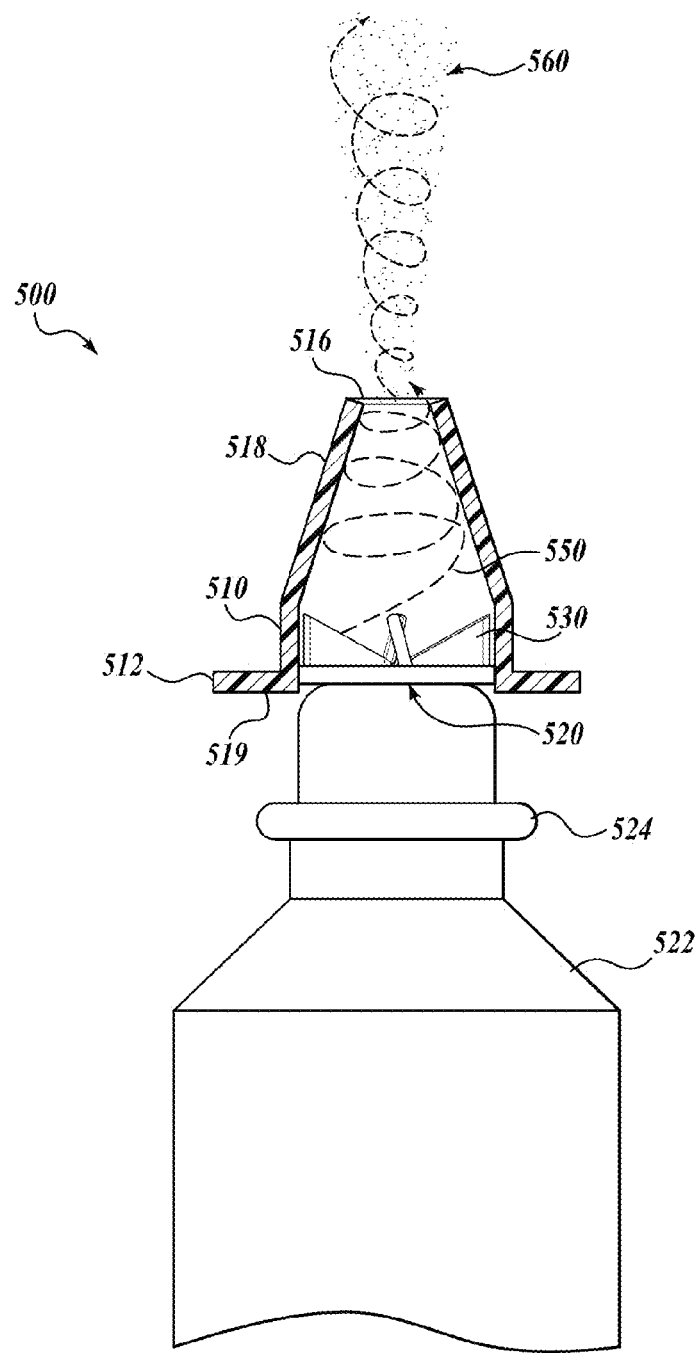
FIG. 5 is a partial cross sectional view of a pressurized olfactory drug delivery device according to a fourth embodiment of the present disclosure.

Referring still to FIG. 4, the device 300 further comprises a second inner cylinder 340 having an exterior surface 341 and interior surface 343, wherein the longitudinal axis of the second inner cylinder 340 is axially aligned with the longitudinal axis of the housing 310. The second inner cylinder 340 extends from a second orifice 342 at the nasal proximal end to an opening 344 at the distal end of the housing 310 that is fluidically connected to a pressurized fluid container 346. The diameter of the second inner cylinder 340 is less than the diameter of the first inner cylinder 322, thereby defining a tubular channel 350 that extends from the distal open end 324 of the first inner cylinder 322 to the first orifice 316. A metering device 348 is fluidically connected to the pressurized fluid container 346 at one end, and to the opening 344 in the distal end of the second inner cylinder 340 at the other end. The interior surface 343 of the cylinder 340 defines a channel 354 that functions as a spin chamber, the channel 354 being connected at one end to the metering device 348 and at the other end to the second orifice 342. A plurality of discharge vents 530 are disposed between the metering device 348 and the interior of the channel 354, the discharge vents 530 being in fluid connection with the metering device 348. The plurality of discharge vents 530, which are better seen with reference to FIGS. 5 and 6, are configured to discharge a pressurized nasal spray having a circumferential axial velocity. In an alternative embodiment, the pressurized fluid container 346 can be substituted with a metered dose inhaler (MDI).

With continued reference to FIG. 4, the manner in which the embodiment of the PODD device 300 described above is used to deliver a pharmaceutical compound to the olfactory epithelium will now be described. A user actuates the pressurized fluid container 346 and metering device 348 to release a predetermined amount of pressurized fluid 360 into the second inner cylinder 340. In the embodiment illustrated in FIG. 4, the pressurized fluid 360 is a pressurized gas. The pressurized gas 360 passes through the metering device 348 and the plurality of discharge vents 530 thereby acquiring a circumferential axial velocity, enters the spin chamber 354, and exits the second orifice 342. As the pressurized fluid 360 leaves the second orifice 342, it creates a partial vacuum which forces fluid up the tubular channel 350. The fluid is aerosolized due to the narrowness of the gap 352 defined by the interior surface 328 of the first inner cylinder 322 and the exterior surface 341 of the second inner cylinder 340. The aerosolized spray is discharged from the first orifice 316 as a spray plume 370 having a circumferential velocity as the aerosol spray 370 enters the nasal cavity. The fluid reservoir 330 preferably is provided with a vent (not shown) to prevent a vacuum that would increase the pressure required to remove fluid from the second orifice 342.

Referring now to FIG. 5, a fourth alternate embodiment of the pressurized drug delivery device 500 will be hereinafter described. The device 500 comprises a cylindrical tubular housing 510 having a longitudinal axis with an outlet 516 located at the proximal end 518 thereof, wherein the proximal end 518 of the housing 510 is preferably conically shaped and functions as a nose cone to enhance user comfort. The housing 510 further comprises flanges 512 located near the distal end that aid in operation of the device by a user. The distal end 519 of the housing 510 is connected to the proximal end member 520 of a pressurized fluid container 522 comprising a metering device 524. The metering device 524 delivers a predetermined amount of fluid, gas or propellant when activated. Alternatively, the pressurized fluid container 522 is an MDI. The metering device may further deliver a predetermined dose of a therapeutic compound provided as a mixture with the pressurized fluid. The device 500 further comprises a plurality of aerosol discharge vents 530 configured to discharge a pressurized nasal spray having a circumferential velocity.

Figure 6A:
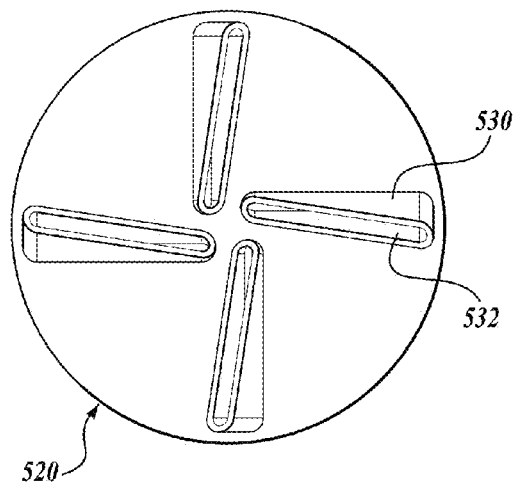
FIG. 6A is an axial view of the nozzle of FIG. 5.
Figure 6B:
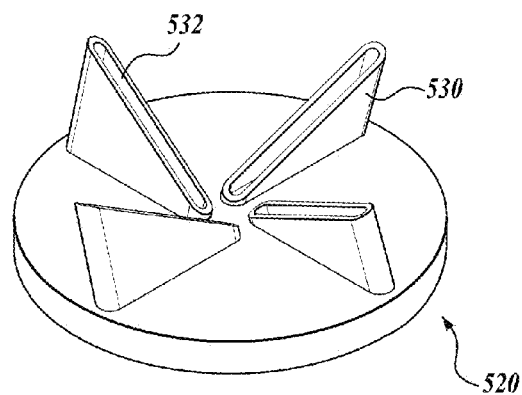
FIG. 6B is an isometric view of the upper portion of the nozzle of FIG. 5.
Figure 6C:
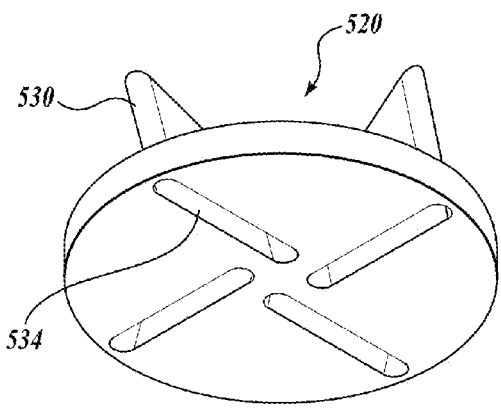
FIG. 6C is an isometric view of the lower portion of the nozzle of FIG. 5.
Figure 7:
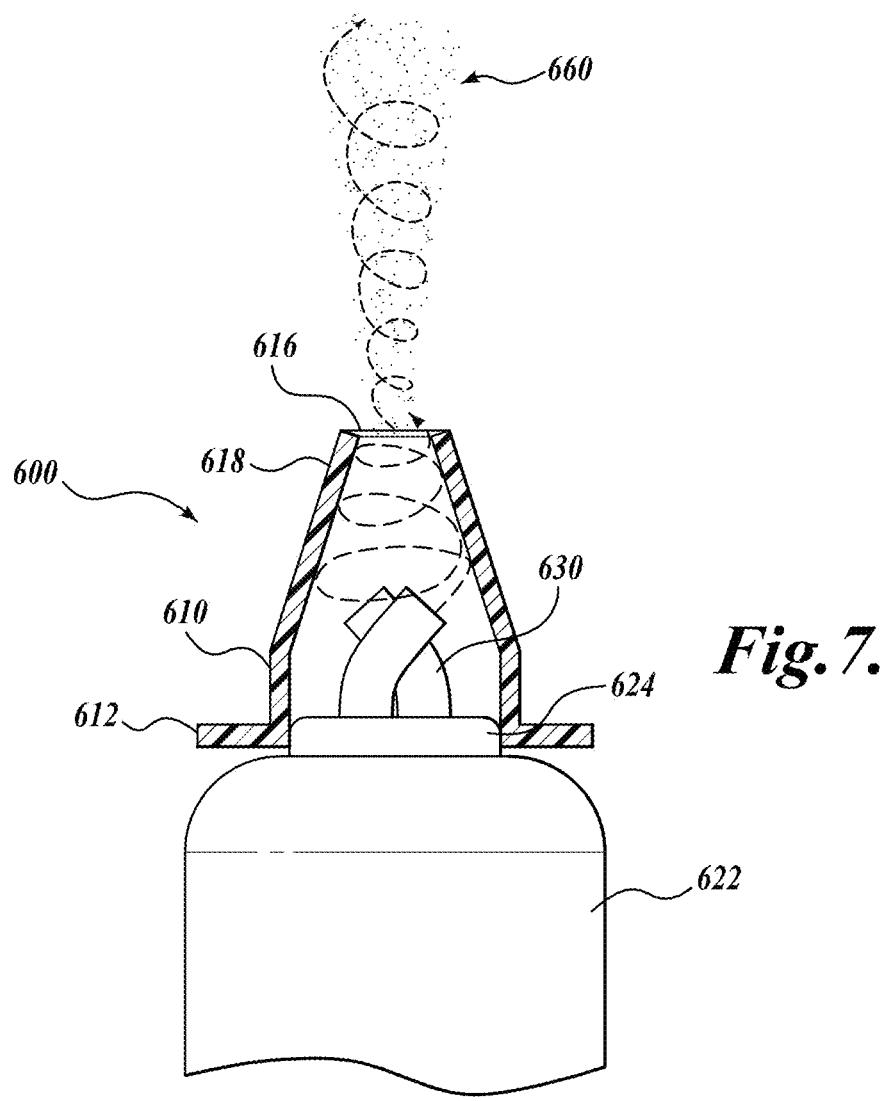
FIG. 7 is a partial cross sectional view of a pressurized olfactory drug delivery device according to a fifth embodiment of the present disclosure.
Figure 8A:
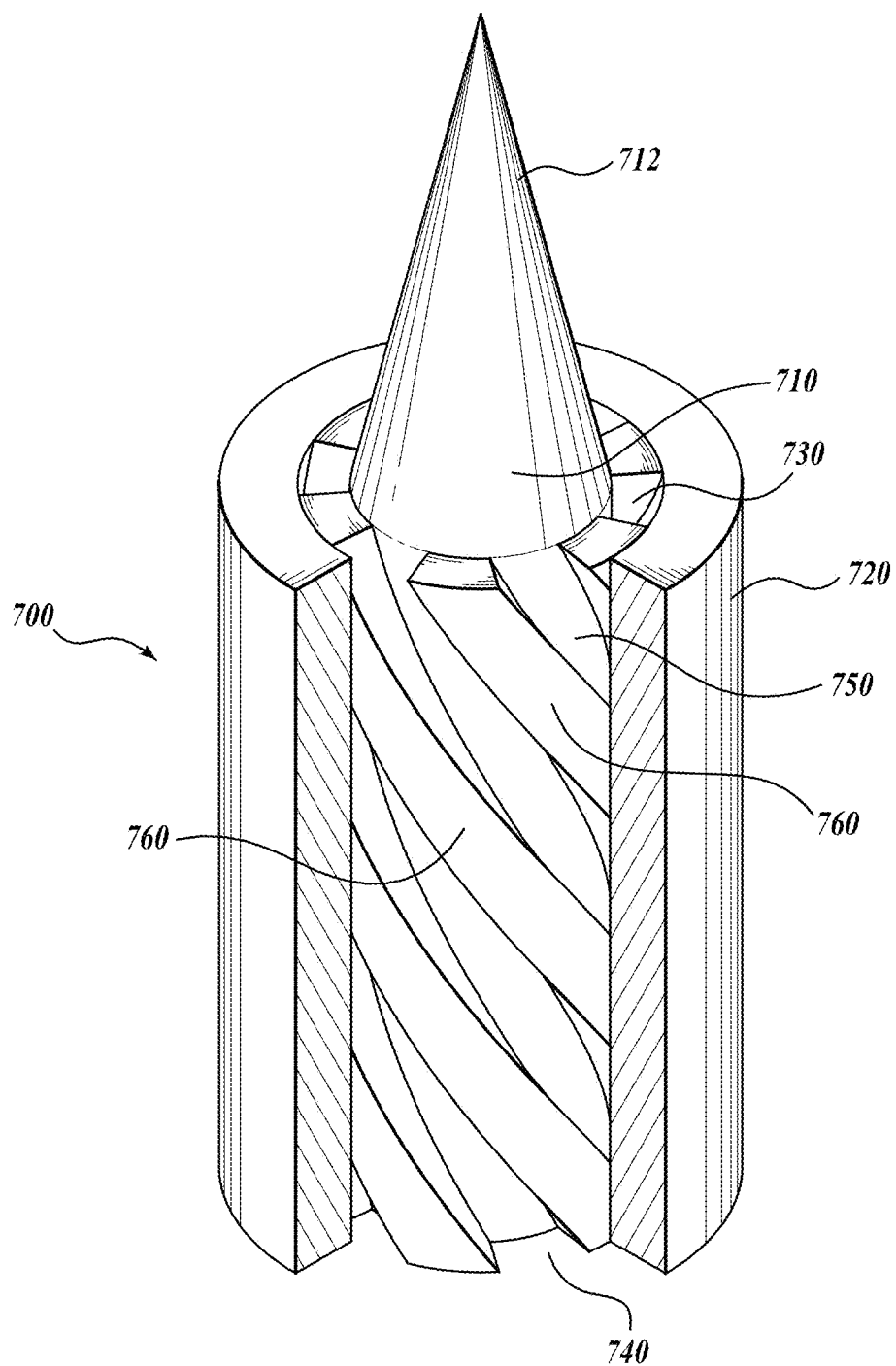
FIG. 8A is a cut-away view of a pressurized olfactory drug delivery device according to a sixth embodiment of the present disclosure.
Figure 8B:
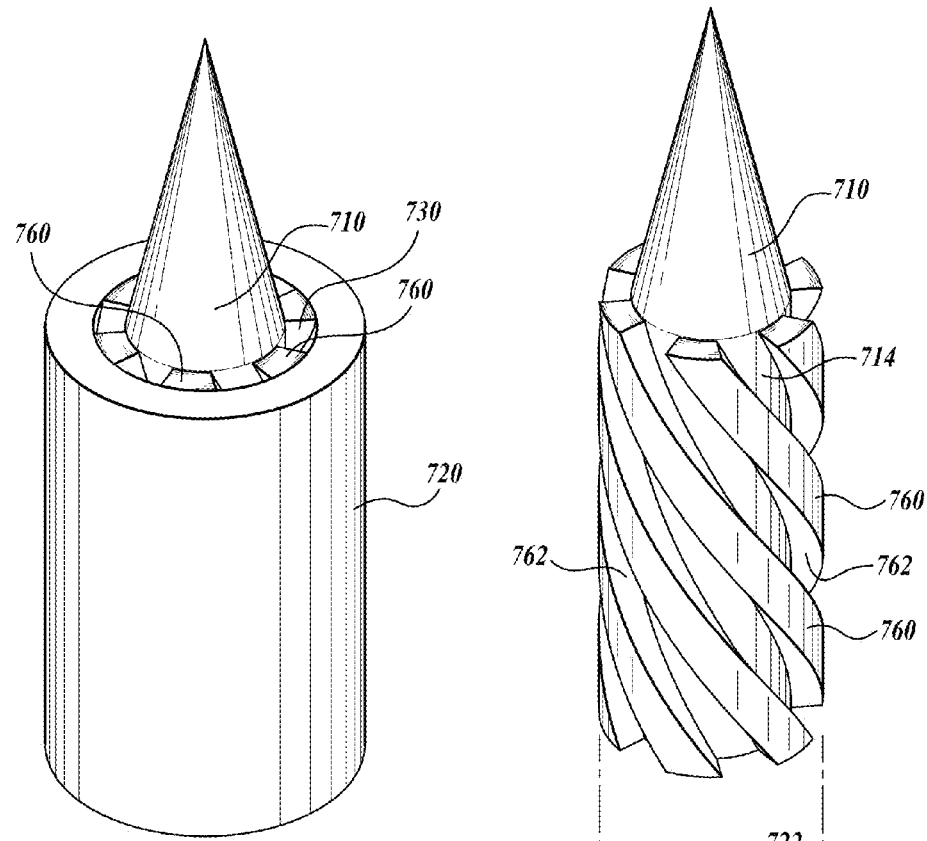
FIG. 8B is a top perspective view of the embodiment of the device shown in FIG. 8A.
Figure 8C:
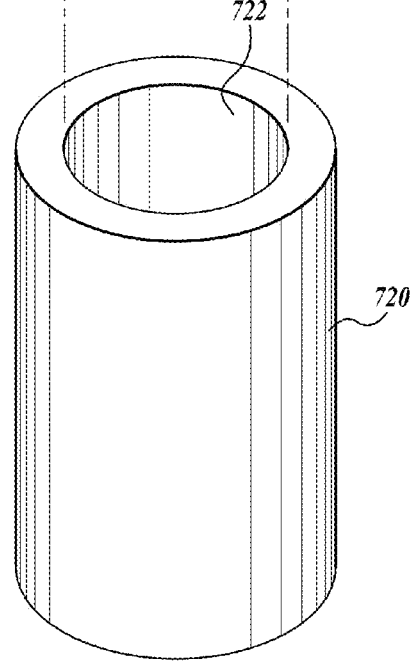
FIG. 8C is an exploded view of the embodiment of the device shown in FIG. 8B.
Figure 8D:
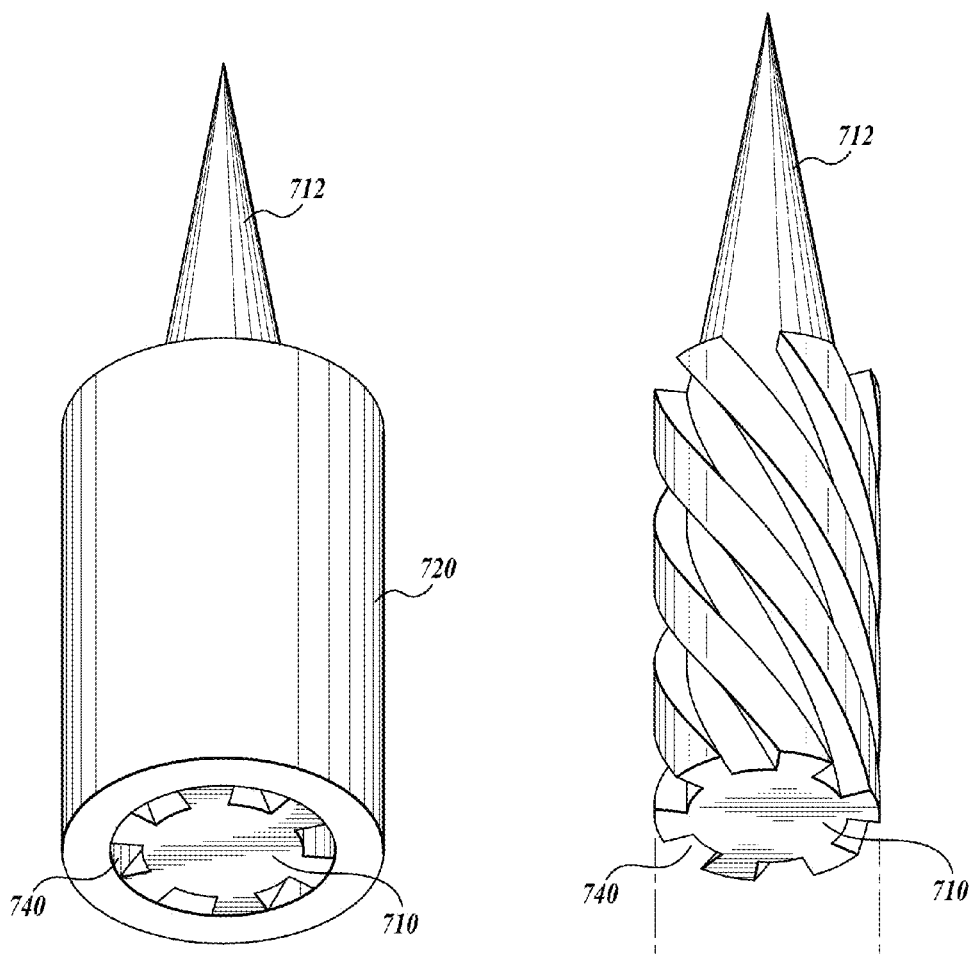
FIG. 8D is a bottom perspective view of the embodiment of the device shown in FIG. 8A.
Figure 8E:
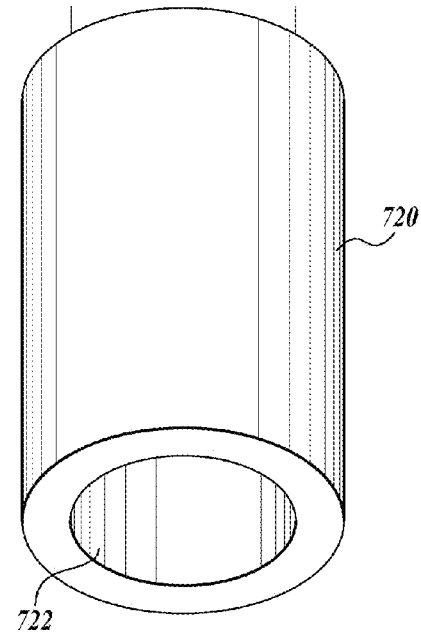
FIG. 8E is an exploded view of the embodiment of the device shown in FIG. 8D.

Referring now to FIGS. 6A-C, the aerosol discharge vents 530 will be described in detail. Each vent 530 has an elongated rectangular or ovoid cross section, and a slit-like or slot-like proximal opening 532 connected to a distal opening 534 by a channel. The vents 530 are oriented generally radially wherein the angle of the proximal-distal axis of each vent 530 is oblique to the longitudinal axis of the device 500 such that an aerosol discharged from the vent has a circumferential and axial component. As shown in FIG. 6C, the distal opening 534 of each vent is fluidically connected to the proximal end member 520 of the pressurized gas container 522. It will be understood that each vent may be constructed such that the vent structure extends above the surface created by the proximal end 520 of the pressurized gas container 522, or, in the alternative, the vents may consist of openings in the proximal end 520 of the pressurized gas container 522, or any other suitable configuration.

Referring now to FIGS. 5 and 6A-C, the manner in which the embodiment of the PODD device 500 described above is used to deliver a pharmaceutical compound to the olfactory epithelium will now be described. A user actuates the pressurized gas container 522 to release a predetermined amount of pressurized gas through the metering device 524 into the distal opening 534 of each vent 530. The pressurized gas exits the proximal opening 532 of each vent as an aerosol 550 having an axial velocity and a radial velocity (only one discharged aerosol 550 is shown for simplicity). The discharged aerosols 550 exiting each vent converge into a single pressurized nasal spray pattern 560 having a circumferential velocity that then exits the device through the outlet 516. The proximal end 518 of the housing 510 serves as a nose cone to aid the user in aligning the device with the nostril to deliver the pressurized nasal spray having a circumferential velocity into the nasal cavity. However, it will be understood that the housing 510 is not required to produce the circumferential velocity of the spray, and that the housing illustrated in FIG. 5 is provided for the convenience of the user. Further, as described in Example 2, flow simulation of the spray pattern produced by a plurality of vents or outlets similar to the embodiment described in FIG. 6 produces a narrow spray plume having circumferential and axial velocity. Therefore, a device having a plurality of outlets as described in a representative embodiment of the present disclosure, such as that illustrated in FIG. 6, does not require a spin chamber or other type of chamber at the proximal end of the device for producing a spray plume having circumferential velocity.

The circumferential velocity created by the plurality of vents has the added advantage that the spray plume is able to penetrate the upper regions of the nasal cavity compared to a spray plume produced without circumferential velocity, and be much more narrow than the wide spray plume produced by a device having a single aerosol source with vortical flow, which further helps the spray to penetrate the upper nasal cavity and contact the olfactory epithelium.

Referring now to FIG. 7, a fifth alternate embodiment of the pressurized drug delivery device 600 will be hereinafter described. The embodiment illustrated in FIG. 7 shares many of the features described above for FIG. 5, including a housing 610 having an outlet 616 surrounded by a conical proximal end 618 that functions as a nose cone. However, instead of a plurality of discharge vents 530, the device 600 comprises a plurality of discharge nozzles 630 fluidically connected to a pressurized fluid container 622 comprising a metering device 624. Alternatively, the pressurized fluid container 622 can be substituted with an MDI. Each nozzle 630 is configured to discharge an aerosol spray in an axial and circumferential direction such that each individual aerosol spray converges into a single pressurized spray pattern 660 having a circumferential velocity. The housing 610 further comprises flanges 612 located near the distal end that aid in operation of the device by a user. As described above, it is understood that the housing 610 is not required to produce the circumferential velocity of the spray.

In the embodiments illustrated in FIGS. 5-7, the pressurized fluid container preferably contains a mixture of compressed fluid and a therapeutic compound. The compressed fluid may be any non-toxic propellant known in the art, for example compressed air, or a pressurized propellant such as chloro fluorocarbon (CFC) or hydrofluoroalkane (HFA).

Referring now to FIG. 8A-E, a delivery device or nozzle 700 for use with a pressurized drug delivery device will be hereinafter described. The nozzle 700 is cylindrically shaped defining a longitudinal axis, and having nasal-proximal end and nasal-distal ends, an inner cylinder portion 710, an outer cylinder portion 720, and a plurality of outlet orifices 730. The plurality of outlets 730 are radially disposed around the longitudinal axis of the nozzle. In one embodiment, the outlets 730 are symmetrically radially disposed around the longitudinal axis of the nozzle. In one embodiment, the plurality of outlets 730 are disposed on a surface at the nasal-proximal end of the nozzle. In one embodiment, at least three outlet orifices 730 are provided. In the embodiment illustrated in FIG. 8A-E, six outlet orifices 730 are provided.

Still referring to the embodiment illustrated in FIG. 8A-E, the inner cylinder 710 has a conical extension 712 disposed at the nasal-proximal end to aid the user in directing a pressurized nasal spray into the nasal cavity. However, it is to be understood that the conical extension 712 is optional and not required for the operation of the nozzle. Further, in some embodiments, the nasal-proximal end of the nozzle may be protected by a nose cone (not shown) to enhance the comfort of the user.

With continued reference to FIG. 8A-E, each outlet orifice 730 is connected to an inlet orifice 740 by an axial channel 750 having a corkscrew, helical or spiral shape. Each channel is an enclosed volume or space defined by the lateral surfaces 762 of corkscrew-shaped axial members 760 that extend along and rotate about the longitudinal axis of the nozzle, the exterior surface 714 of the inner cylinder portion 710, and the interior surface 722 of the outer cylinder portion 720.

The nozzle 700 may be constructed by machining threads or grooves in the exterior surface 714 of the inner cylinder portion 710 to produce the corkscrew shaped axial members 760 thereof. Alternatively, the nozzle 700 may be constructed by machining threads or grooves in the interior surface 722 of the outer cylinder portion 720 to produce the corkscrew shaped axial members 760 thereof. It is understood that the nozzle is not limited by the method of producing or manufacturing the nozzle.

In a preferred embodiment, the cross-sectional area of the channel decreases from distal to proximal, such that the outlets 730 are smaller than the inlets 740, thereby providing acceleration to a pressurized fluid entering the channel. It will be understood that the channels may be round, square, rectangular, ovoid, or any other suitable shape in cross section. The outlets 730 are configured such that a pressurized fluid discharged from the outlet has an axial velocity and a circumferential velocity. The outlets 730 are further configured to atomize the pressurized fluid into an aerosol spray as the pressurized fluid exits the outlets 730. Further, in some embodiments, the outlets 730 are configured such that the aerosol spray discharged from the outlet is further directed radially inwardly at an oblique angle toward the longitudinal axis of the nozzle.

Referring again to FIGS. 8A-E, the manner in which the embodiment of the nozzle 700 described above is used to deliver a pharmaceutical compound to the olfactory epithelium of a human or animal subject will now be described. In one embodiment, the nozzle 700 will be attached to a pressurized fluid container (not shown) containing a mixture of pressurized fluid and a therapeutic compound or pharmaceutical composition. In other embodiments, pressurized fluid container comprises a metering device that provides a predetermined amount of pressurized fluid comprising a predetermined dosage of a therapeutic compound when activated. In a preferred embodiment, the pressurized fluid container is a metered dose inhaler. The pressurized fluid may be a compressed gas, such as compressed air, or a propellant known in the art. In operation, pressurized fluid discharged from the pressurized fluid container enters the plurality of inlets 740, travels through the axial channels 750 and exits the outlets 730. The pressurized fluid becomes atomized into an aerosol spray discharge as it exits the outlets 730. After exiting the outlets 730, each individual aerosol spray discharge converges into a single spray pattern having circumferential velocity. In a preferred embodiment, the nasal-proximal end of the nozzle is partially inserted into the nasal cavity of the human or animal subject, and the single spray plume maintains circumferential velocity as it exits the device and enters the nasal cavity. It is understood that the nozzle 700 disclosed herein has the advantage that no spin chamber or other type of chamber is required to induce the circumferential axial velocity of the aerosol spray plume; the circumferential flow is induced solely by the configuration of the axial channels 750 and the outlets 730.

The circumferential velocity created by the plurality of outlets 730 has the added advantages that the spray plume is able to penetrate the upper regions of the nasal cavity compared to a spray plume produced without circumferential velocity, and is much narrower than the wide spray plume produced by a device having a single aerosol source with vortical flow. The narrow spray plume, in combination with the circumferential velocity provided by the nozzle 700, allows the aerosolized spray to penetrate the upper nasal cavity and deposit therapeutic compounds on the olfactory epithelium. Representative methods for measuring the diameter of the spray plume are described in Example 1.

In some embodiments, the device of the disclosure discharges a plurality of particles having an average or mean diameter in the range selected from the group consisting of about 1 to about 100 micrometers, about 5 to about 50 micrometers, about 5 to about 30 micrometers, about 5 to about 25 micrometers, about 5 to about 20 micrometers, about 5 to about 15 micrometers, and about 10 to about 15 micrometers. In some embodiments, at least 70%, at least 80%, at least 90% and at least 95% of the particles produced by the device have a diameter between about 5 and 25 micrometers. In one embodiment, the majority of the particles discharged by the device are in the range of about 5 to 20 micrometers. Aerosol discharge outlet diameters for producing the desired particle sizes are typically in the range of 01. to 0.5 mm.

The disclosure further provides a method for depositing a therapeutic compound on the olfactory epithelium in the nasal cavity of a human or animal subject. In one embodiment, the method comprises administering the therapeutic compound from a pressurized nasal spray device into the nasal cavity, wherein the pressurized nasal spray device comprises an aerosol outlet that discharges a pressurized spray comprising the therapeutic compound, the pressurized spray having a circumferential velocity as it exits the outlet and enters the nasal cavity.

In another embodiment the method comprises administering a pressurized fluid comprising the therapeutic compound from a pressurized olfactory drug delivery device into the nasal cavity, wherein the device comprises a plurality of outlets that discharge a plurality of pressurized aerosol sprays comprising the therapeutic compound, the plurality of pressurized aerosol sprays converging into a single spray plume having a circumferential velocity after exiting the device. In one embodiment, each outlet of the device is located at the nasal-proximal most end of the device and discharges the aerosol spray having a circumferential velocity directly into the nasal cavity.

In some embodiments, the method administers a plurality of particles to the nasal cavity, the plurality of particles having an average or mean diameter in the range selected from the group consisting of about 1 to about 100 micrometers, about 5 to about 50 micrometers, about 5 to about 30 micrometers, about 5 to about 25 micrometers, about 5 to about 20 micrometers, about 5 to about 15 micrometers, and about 10 to about 15 micrometers. In other embodiments, at least 70%, at least 80%, at least 90% and at least 95% of the particles administered by the method have a diameter between about 5 and 25 micrometers. In one embodiment, the majority of the particles administered by the method are in the range of about 5 to 20 micrometers.

In one embodiment, the device used in the method comprises a metered dose device that releases a predetermined amount of the pressurized fluid comprising a predetermined dose of the therapeutic compound when the device is activated. In this embodiment, the method delivers about 40% of the predetermined amount of the pressurized fluid that enters the nasal cavity as an aerosol spray to the olfactory epithelium. In other embodiments, the method delivers at least about 40% of the predetermined dose of the therapeutic compound to the olfactory epithelium. In one embodiment, the method results in higher concentrations of a therapeutic compound in the brain than in the blood.

In some embodiments, the therapeutic compound of the method is provided as part of a composition or formulation containing stabilizers, preservatives, or additives that are well known in the art. Further, in some embodiments, the therapeutic compound may be formulated with colloids, nanoparticles, liposomes, micelles, or another type of suspension.

While not wishing to be bound by theory, the devices and methods described in the above embodiments are believed to improve the penetration of an aerosol spray into the upper nasal cavity by displacing the resident or residual air volume present in the upper naval cavity. This allows a larger fraction of the therapeutic compound to be deposited directly on the olfactory epithelium while at the same time reducing the amount of the therapeutic compound that is deposited on the respiratory epithelium, esophagus, stomach and lungs. A further advantage of the devices described in the present disclosure is a reduction in the back pressure required to deliver drugs to the olfactory epithelium when compared to devices that deliver a narrow spray plume without a corresponding centrifugal velocity component.

EXAMPLE 1

This example describes various functional parameters of the device illustrated in FIGS. 1 and 2.

The spray rate was tested by varying the driving pressure from 1 to 6 pounds per square inch and the diameter of the orifice 154. The spray rates were reproducible and within the desired range for human application, namely less than 50 microliters per second.

Figure 9:
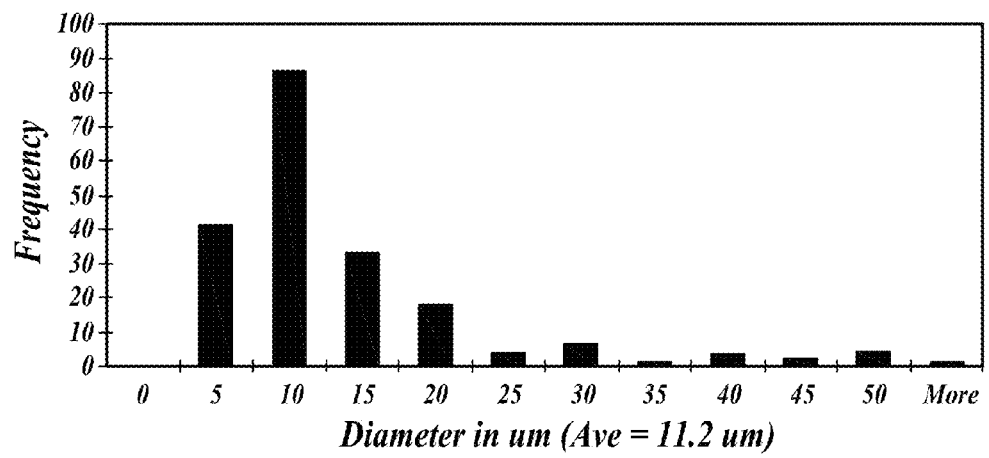
FIG. 9 is a graph illustrating the particle size produced by a device of the present disclosure, as described in Example 1.

FIG. 9 shows the particle size distribution when water was sprayed from the device into viscous oil at a distance of 2 cm and 4 psi, and the resulting droplet diameters were measured using a microscope with size analysis software. A total of 199 measurements were made. The distribution shows that the device produces particles having diameters of from 5 to greater than 50 microns, and that the majority of the particle diameters are between 5 and 20 micrometers, with an average diameter of 11.2 microns. The size distribution obtained by this method of atomization is therefore desirable for nasal spray applications.

Figure 10:
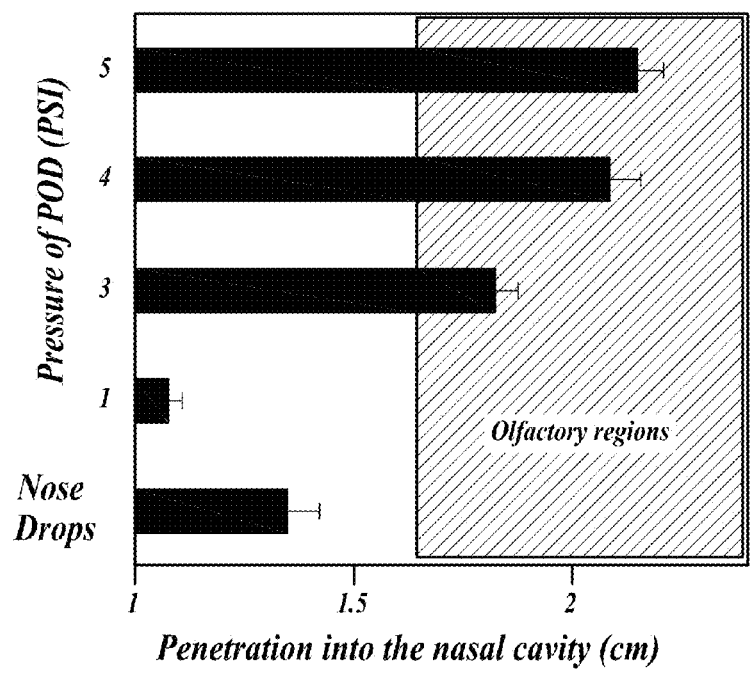
FIG. 10 is a graph illustrating the penetration of blue dye into the nasal cavity of rats administered using a device according to one embodiment of the present disclosure, wherein the dye was administered from the device at different air pressures, and each horizontal bar represents the mean value for 4-6 rats and the error bars represent standard deviation, as described in Example 1.

FIG. 10 shows the penetration of an aerosolized blue dye into the nasal cavity of rats using the device illustrated in FIGS. 1 and 2 compared to the penetration of nose drops. Rats have a maximum naval cavity distance of about 2.5 cm. Increasing the air pressure of the device increases the penetration into the nasal cavity and coverage of the olfactory epithelium. The nasal drops resulted in no deposition on the olfactory epithelium, while the 3 psi spray from the PODD resulted in approximately 15% deposition on the olfactory epithelium, and the 4 psi spray from the PODD resulted in approximately 40% deposition on the olfactory epithelium. The results presented in FIG. 10 indicate that between 3-5 psi, a maximum penetration in nasal cavity is achieved to produce an optimal result. Higher pressures were untested but could lead to even deeper penetration into the nasal cavity.

Figure 11:
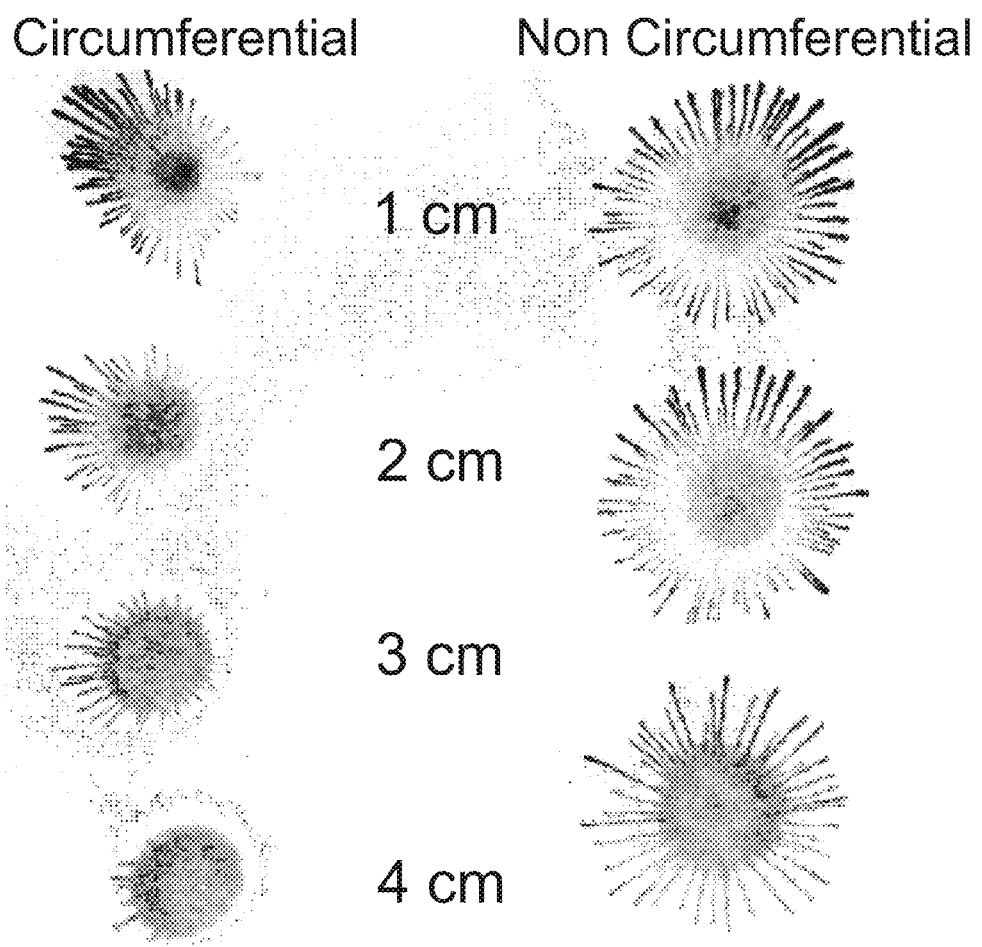
FIG. 11 is a series of photographs illustrating the spray pattern produced by a device of the present disclosure on the left hand side, and a device that does not impart a circumferential velocity to the spray pattern on the right hand side, as described in Example 1.

FIG. 11 shows the spray pattern produced by the device using a blue dye marker sprayed out of the device at various distances from a piece of paper. The left-hand side of FIG. 11 illustrates the circumferential flow as the angle of the majority of the dye shifts radially as the distance from the nozzle changes. The right-hand side of FIG. 11 illustrates the symmetrical pattern produced by a spray nozzle that does not impart a circumferential velocity to the aerosol spray.

Table 1 shows the delivery of the antiviral drug nelfinavir to different brain regions in rats using nose drops (which approximates nasal distribution with a standard nasal spray) or the PODD device illustrated in FIGS. 1 and 2. 30 minutes after delivery, the PODD device delivered 42.7% of the drug dose present in the nasal spray to the olfactory epithelium compared to 4.7% of the dose delivered by nose drops. The drug concentrations were higher in various brain regions and lower in the blood when delivered using the PODD device.

TABLE 1

Distribution of nelfinavir in rats 30 minutes after delivery via nose drops or using a pressurized olfactory drug delivery device of the present disclosure.

| | Nelfinavir concentration (nmol/g tissue) | |
|---|---|---|
| | drops | POD |
| olfactory bulbs | 0.137 ± 0.104 | 0.409 ± 0.057 |
| cortex | 0.011 ± 0.003 | 0.083 ± 0.008 |
| diencephalon | 0.069 ± 0.027 | 0.205 ± 0.02 |
| cerebellum | 0.071 ± 0.008 | 0.302 ± 0.073 |
| brainstem | 0.087 ± 0.026 | 0.117 ± 0.052 |
| blood | 0.0159 ± 0.025 | 0.053 ± 0.010 |
| olfactory delivery | 4.7% | 42.7% |

The results presented in this Example show that the device and methods disclosed in the application are useful for delivering therapeutic compounds to the olfactory epithelium and brain regions, and that a large fraction of the dose present in nasal spray having a circumferential velocity is deposited on the olfactory epithelium. The results also show that the device delivers a high fraction of drug to the olfactory epithelium, which leads to higher drug concentrations in the brain and lower drug concentrations in the systemic circulation.

EXAMPLE 2

This example demonstrates the improved penetration of a simulated nose cone using a device comprising a plurality of outlets in comparison to a device having a single outlet with and without circumferential flow.

Methods:

Flow simulations were carried out using the Star-CCM+ computational fluid dynamics simulation software package (CD-adapco), version 3.06.006. In the simulation, a cone was used with similar geometry to a nasal cavity for the sake of simplicity. The cone was designed to be narrow towards the top with the only outlet for residual air located at the bottom of the cone. Thus, the air in the top of the cone was stagnant and had to be displaced in order for the nozzle flow to penetrate the top of the cone, much like the upper nasal cavity of a human. The dimensions of the cone were 7.5 cm from top to bottom, in order to realistically simulate nasal delivery to the olfactory epithelium of a human.

The following nozzle structures were tested:

(1) a nozzle without circumferential flow and a single outlet;

(2) a nozzle with circumferential flow and a single outlet; and (3) a nozzle with circumferential flow and a plurality of outlets, in accordance with an embodiment of a device of the present disclosure as illustrated in FIG. 6;

The various nozzle structures were place in the bottom of the cone with the outlets pointed upward towards the top of the cone. The area of flow for each of the nozzles was kept at 3.54 mm$^2$ and the air velocity coming from the outlets was kept constant at 60 m/s. The simulation was performed under a steady time condition with k-epsilon turbulence. The simulations were run between 115 to 370 iterations until the momentum residuals remained constant between iterations.

Results:

The results of the flow simulations are shown in FIGS. 12A-12D.

Figure 12A:
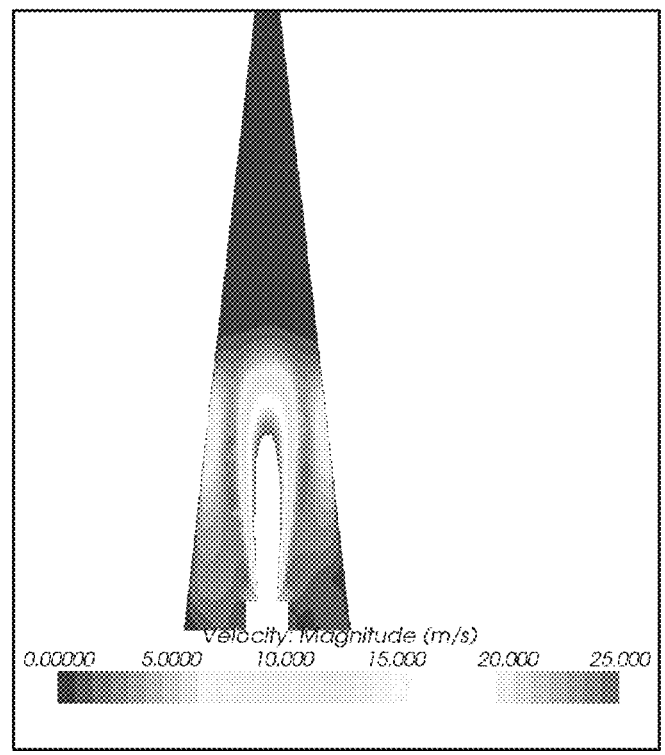
FIG. 12A shows the simplex air flow pattern and velocity of the spray from a flow simulation using an outlet without circumferential velocity in a flow simulation, demonstrating poor penetration of the cone, as described in Example 2.

FIG. 12A shows the simplex air flow pattern and velocity of the spray from a flow simulation using nozzle structure (1) having an outlet without circumferential velocity. As shown in FIG. 12A, the simplex flow does a poor job of penetrating the cone because it cannot move the air in the narrow top of the cone, so the plume gets pushed off to the sides.

Figure 12B:
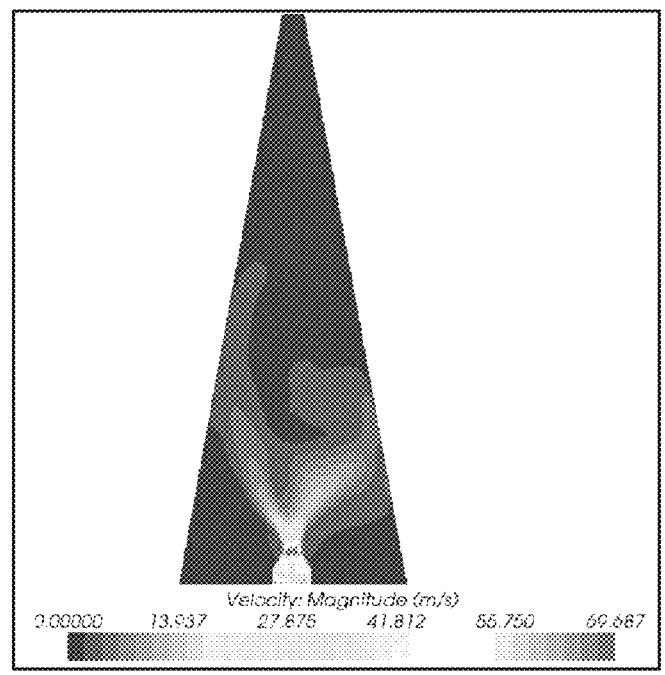
FIG. 12B shows the circumferential flow pattern and velocity of the spray from a flow simulation using a nozzle with a single outlet with circumferential movement, demonstrating poor penetration of the cone, as described in Example 2.

FIG. 12B shows the circumferential flow pattern and velocity of the spray from a flow simulation using nozzle structure (2) having an single outlet with circumferential velocity. As shown in FIG. 12B, the spray flow coming out of the nozzle structure (2) having a single outlet with circumferential velocity does not penetrate into the cone either because a flow with vortical flow coming out of one orifice tends to spread out when exiting the orifice.

Figure 12C:
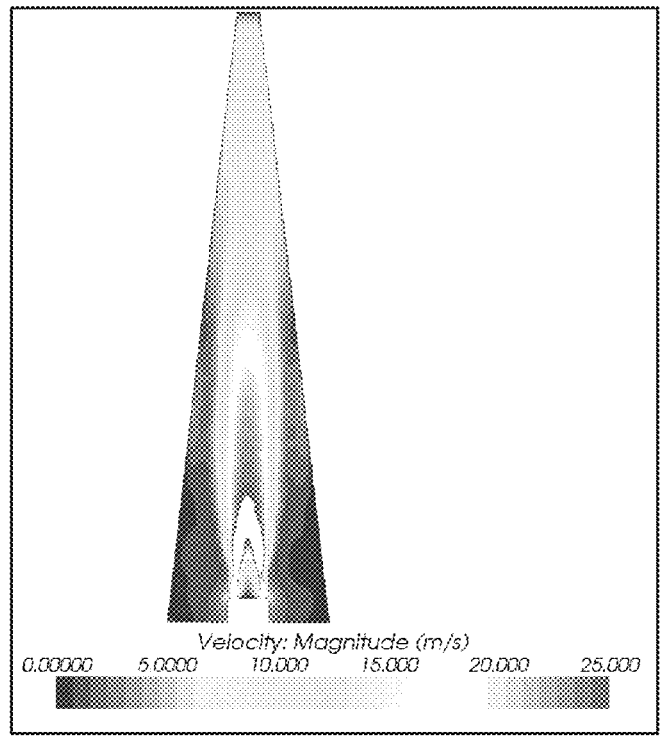
FIG. 12C shows the rotational flow pattern and velocity of the spray from a flow simulation using an embodiment of a device of the present disclosure illustrated in FIG. 6, demonstrating improved penetration of the cone due to a narrow spray with circumferential and axial velocity, as described in Example 2.

FIG. 12C shows the circumferential flow pattern and velocity of the spray from a flow simulation using nozzle structure (3) having a plurality of outlets with circumferential velocity, in accordance with an embodiment of a device of the present disclosure as illustrated in FIG. 6. As shown in FIG. 12C, the spray flow has improved penetration of the cone and penetrates to the top of the cone due to its narrow spray plume having circumferential and axial velocity, which allows for displacement of the air in the upper nasal cavity.

Figure 12D:
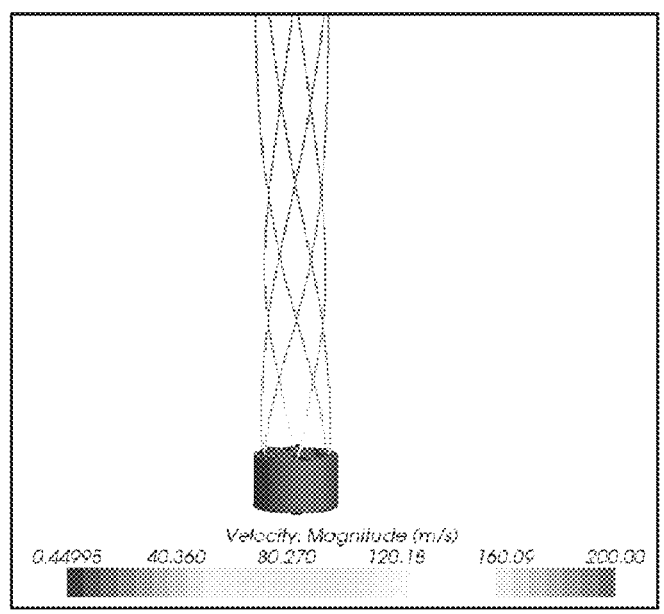
FIG. 12D illustrates the flowstreams from the spray pattern shown in FIG. 12C.

FIG. 12D illustrates the flowstreams from the spray pattern shown in FIG. 12C.

The flow simulation comparison using the various nozzle structures described in this example demonstrates the advantages of using a nozzle having a plurality of outlets which generates a narrow spray pattern having circumferential velocity to penetrate a narrow area, such as the upper nasal cavity of a human, where the air must be displaced to allow for penetration of the spray in order to deposit a large fraction of drug on the olfactory epithelium.

While illustrative embodiments have been illustrated and described, it will be appreciated that various changes can be made therein without departing from the spirit and scope of the invention.

The embodiments of the invention in which an exclusive property or privilege is claimed are defined as follows:

1. A pressurized olfactory drug delivery device comprising:
    (a) a container comprising a mixture of a pressurized fluid and a therapeutic compound, the container at a distal end of the pressurized olfactory drug delivery device;
    (b) a nozzle delivery device defining a longitudinal axis and having:
        (i) an inner axial member having a cylindrical core,
        (ii) a plurality of helical channels, the helical channels having a radial dimension, a basal surface, and an apical surface, wherein the basal surface is in contact with an outer surface of the axial member, and
        (iii) an outer cylindrical member in contact with the apical surface of the helical channels, and
    (c) a metering device configured for selectively discharging the mixture of a pressurized fluid and a therapeutic compound through the helical channels;
    wherein each helical channel comprises an inlet for receiving the mixture of a pressurized fluid and a therapeutic compound, and an outlet for discharging the mixture of a pressurized fluid and a therapeutic compound, the outlets being located at a proximal-most end of the pressurized olfactory drug delivery device, each outlet is configured to produce an aerosol spray having an axial velocity and circumferential velocity, such that the axial velocity and the circumferential velocity produced by each outlet converge into a single spray plume having a circumferential velocity.

2. The pressurized olfactory drug delivery device of claim 1, further comprising a conical extension, the conical extension located at the proximal-most end of the pressurized olfactory drug delivery device and congruent with the inner axial member.

3. The pressurized olfactory drug delivery device of claim 1, wherein the helical channels spiral around the longitudinal axis.

4. The pressurized olfactory drug delivery device of claim 1, wherein the therapeutic compound comprises at least one of small molecules, peptides, proteins, antibodies, antibody fragments, aptamers, or nucleic acids.

5. The pressurized olfactory drug delivery device of claim 1, wherein the device delivers liquid or lyophilized therapeutic compounds.

6. The pressurized olfactory drug delivery device of claim 1, wherein the therapeutic compound is delivered as a formulation comprising stabilizers, preservatives, or additives.

7. The pressurized olfactory drug delivery device of claim 1, wherein the therapeutic compound is delivered as a formulation comprising colloids, nanoparticles, liposomes, or micelles.

* * * * *